United States Patent [19]

Lentz

[11] Patent Number: 5,522,881
[45] Date of Patent: Jun. 4, 1996

[54] IMPLANTABLE TUBULAR PROSTHESIS HAVING INTEGRAL CUFFS

[75] Inventor: David J. Lentz, Randolph, N.J.

[73] Assignee: Meadox Medicals, Inc., Oakland, N.J.

[21] Appl. No.: 267,468

[22] Filed: Jun. 28, 1994

[51] Int. Cl.$^6$ ................................. A61F 2/06; A61F 2/04
[52] U.S. Cl. ................... 623/1; 623/11; 623/66; 606/191
[58] Field of Search ........................... 623/1, 2, 11, 12, 623/66; 604/93–96; 606/191, 198

[56] References Cited

U.S. PATENT DOCUMENTS

| | | | |
|---|---|---|---|
| 3,868,956 | 3/1975 | Alfidi et al. | 260/24 |
| 4,140,126 | 2/1979 | Choudhury | 623/1 |
| 4,141,364 | 2/1979 | Schultze | 623/1 |
| 4,655,771 | 4/1987 | Wallsten | 623/1 |
| 4,705,517 | 11/1987 | Di Pisa, Jr. | 623/1 |
| 4,728,328 | 3/1988 | Hughes et al. | 623/1 |
| 4,787,899 | 11/1988 | Lazarus | 623/1 |
| 5,122,154 | 6/1992 | Rhodes | 623/1 |
| 5,151,105 | 9/1992 | Kwan-Gett | 623/1 |
| 5,163,958 | 11/1992 | Pinchuk | 623/1 |

Primary Examiner—David Isabella
Attorney, Agent, or Firm—Hoffmann & Baron

[57] ABSTRACT

An implantable tubular prosthesis having cuffs adapted to accommodate stents. The prosthesis includes a hollow tubular conduit with cuffs at each end. Each of the cuffs has a closed end and a open end to create a slot for housing the stents. The prosthesis may be an implantable tubular intraluminal prosthesis for insertion within a body vessel, where the hollow tubular conduit is radially expandable to buttress the body vessel. Alternatively, the prosthesis may be an implantable tubular prosthetic graft for surgical replacement of damaged or diseased existing body vessels. The tubular prosthesis and stent combination may be radially expanded so that the stents anchor the prosthesis within the lumen. The slots which house the stents, prevent contact between the stents and fluids flowing through the body vessel.

22 Claims, 2 Drawing Sheets

IMPLANTABLE TUBULAR PROSTHESIS HAVING INTEGRAL CUFFS

FIELD OF THE INVENTION

The present invention relates generally to an implantable tubular prosthesis. More particularly the present invention relates to an implantable tubular prosthesis adapted to accommodate stents for supporting the prosthesis.

BACKGROUND OF THE INVENTION

The implantation of synthetic tubular prostheses to replace or buttress damaged or diseased vascular vessels or other luminal passageways within the human body is known. Synthetic tubular prostheses include grafts as well as endoprosthetic devices.

Tubular prosthesis such as grafts, are typically implanted by surgical techniques. The surgeon would suture the graft in place in the blood vessel or other body passageway. Other endoprosthetic devices may be implanted intraluminally. These devices may be inserted percutaneously by use of a delivery catheter. Obviously, percutaneous catheter delivery permits implantation of a prosthesis without the need for major surgical intervention and the risks inherent therewith. The art therefore is moving toward the increased use of intraluminal implantation of various prosthetic devices. It has been found that under certain conditions, grafts as well as endoprosthetic devices may be implanted by means of a delivery catheter.

With respect to grafts and other prostheses which may be traditionally surgically implanted, means other than suturing must be found to secure these prostheses in place in the body passageway in order to effectively permit intraluminal implantation. It has been known to employ stents in combination with grafts and various other prostheses to support and secure a prosthesis in place in the body passageway after implantation. Stents are typically radially expandable and/or contractible support members which are positioned inside of the graft or other tubular prosthesis and once the tubular prosthesis is properly positioned, the stent would be expanded to anchor the prosthesis within the body passageway.

However, the use of stents to anchor prostheses is not without problems. Stents sometimes migrate with the flow of body fluid within a vessel if undersized or underexpanded. Also, thrombosis or fibrin buildup may occur within the stent diminishing patency of the intraluminal passageway when the stent is in direct contact with the blood.

U.S. Pat. No. 5,151,105 discloses an implantable, collapsible tubular prosthesis, i.e., graft, for surgical implantation within a vascular organ. The ends of the prosthesis include collapsible circular stents or annular balloons affixed thereto. The stents expand to seal the ends of the endovascular prosthesis to the inner luminal surface of the blood vessel into which the prosthesis is implanted. The stents may be sutured to the interior wall such that they are in direct contact with the body fluid therein, or may be placed within annular pockets. Because of the nature of the placement of the stent within the annular pocket, the insertion must take place before implantation. If problems arise surrounding the size of the stent, the tubular prosthesis into which the stent has been sealed must be replaced with a more closely fitting stent.

U.S. Pat. No. 4,728,328 discloses an implantable tubular prosthetic graft having prosthesis cuffs formed on distal ends of the graft. The cuffs are formed by folding the edges of the graft back over itself and bonding the turned back edges to the graft body. These cuffs are then used to suture the graft to the host vessel. Under certain conditions, however, grafts require greater support than that afforded by merely suturing through cuffs positioned at opposing ends of such graft. Also, the need for suturing would preclude catheter delivery.

Accordingly, there is a need for an implantable tubular prosthesis which overcomes the aforementioned shortcomings of the prior art and provides a universal fitting means for cooperatively employing a stent in combination with the tubular prosthesis.

SUMMARY OF THE INVENTION

In accordance with the present invention, an implantable, tubular prosthesis is provided that is adapted to be used universally with a stent. The implantable tubular prosthesis includes a tubular conduit which is capable of radial diametrical change. The prosthesis also includes at least one cuff positioned at one end of the conduit. A variable diameter stent is held or housed by the cuff.

Preferably, the tubular conduit is ribbed longitudinally to permit folding and insertion into a lumen using a catheter. Alternatively, the tubular conduit may be crimped longitudinally to permit folding and insertion into the lumen. The tubular conduit may comprise a braided, knitted or woven fabric, and may be radially self-expanding to conform to a shape and inner surface of a lumen into which it is implanted.

The present invention may include an implantable tubular prosthetic graft or may include an endoprosthetic or intraluminal device.

The present invention also includes a method for repairing a damaged location of a body vessel that includes the steps of providing a hollow tubular conduit having cuffs at the ends thereof. A pair of stents is provided. The tubular conduit is implanted in the body vessel to span the damaged location. The stents are inserted into the cuffs and the cuffs are expanded to anchor the conduit in the body vessel on each side of the damaged location. The stents may be inserted into the cuffs prior to implantation of the conduit. Alternatively, the stents may be inserted into the cuffs after implantation.

DETAILED DESCRIPTION OF THE PREFERRED EMBODIMENTS:

The implantable tubular prosthesis having integral cuffs of this invention may be used as an intraluminal conduit or endoprosthesis for percutaneous implantation within a diseased or damaged blood vessel or other like vessel to provide reinforcement and support to the vessel. The implantable tubular prosthesis may also be used as a vascular graft to replace damaged or diseased portions of blood vessels or like fluid passageways. The present invention contemplates catheter delivery of the prosthesis, however the invention is not limited thereto.

Figure 1:
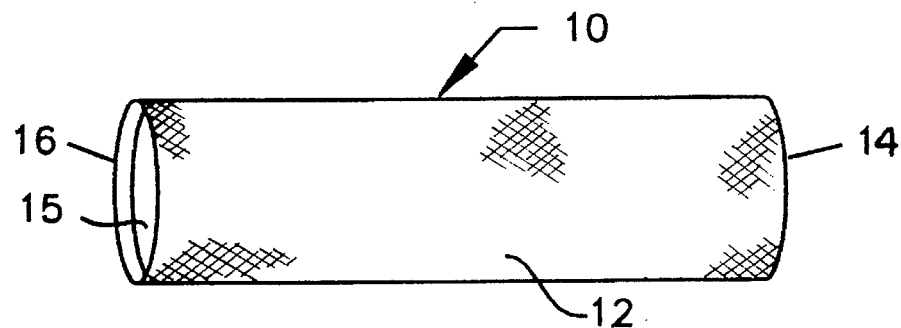
FIG. 1 is a perspective showing of a synthetic tubular prosthesis.

Referring to FIG. 1, an implantable tubular prosthesis 10 is shown. Prosthesis 10 includes tubular conduit 12 having first and second ends 14 and 16 and a tubular channel 15 therebetween. Tubular prosthesis 10 may be a textile member formed from braided, knitted or woven synthetic yarns. Additionally, extruded tubes made from polytetrafluoroethylene (PTFE) and the like may also be used. Preferably the prosthesis 10 may be formed from a polymer material such as polypropylene. While the above-described materials are examples of materials used to form tubular prosthesis 10, it is of course understood that the present invention may be formed of any suitable material. As will be described in further detail hereinbelow, tubular prosthesis 10 may be radially compressed from the structure shown in FIG. 1 so as to permit insertion into a delivery catheter for implantation within a body passageway such as a blood vessel, whereupon the prosthesis is expanded to its original form for secure deployment therein. Alternatively, tubular prosthesis 10 may be constructed to be of expandable material so that it is catheter-insertable in its original state and once positioned within the body passageway may be radially expanded (or radially self-expanded) for deployment in the vessel.

Figure 2:
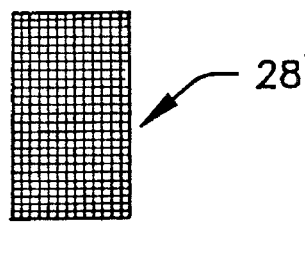
FIGS. 2 and 3 are side elevational and front views respectively of a stent used in accordance with the present invention.
Figure 3:
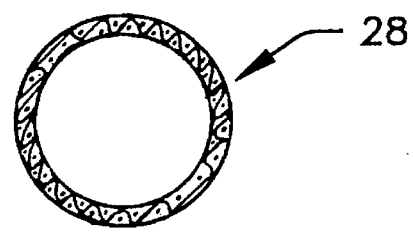

Referring now to FIGS. 2 and 3, a stent 28 is shown. Stent 28 is generally an annular member capable of radial expansion between a first diameter and a second diameter different from the first diameter. Stents such as these are well known in the art may be formed from materials such as stainless steel or other metals or alloys, polymeric materials or composites of polymers and metal and may be shaped in the form of springs, helically-wound coil springs, wire mesh or other structures and configurations. Coil springs and the like may also be manufactured from any expandable heat-sensitive material.

For example, U.S. Pat. No. 4,655,771 discloses an expandable device made from woven stainless steel wire. Another example of an expandable stent is disclosed in U.S. Pat. No. 3,868,956. The stent disclosed therein that is formed with a specific type of metal alloy displaying a memory function. That is, the alloy with which the stent is formed has the ability when compressed to recover its initial non-compressed shape upon heating. Such a stent can be compressed, inserted into and transported within a blood vessel to a desired position. Once in position, the stent can be heated for expansion to its original non-compressed state.

In the present illustrative embodiment, a wire mesh stent is shown. The stent 28 is capable of being radially compressed from the condition shown in FIGS. 2 and 3 so that it may be intraluminally deployed along with or subsequent to insertion of tubular prosthesis 10. While a compressible stent is shown, it is contemplated that a stent which is radially expandable from an original state may also be employed.

In the preferred embodiment of the present invention tubular prosthesis 10 includes longitudinally extending ribs 18 (FIG. 5) to permit folding or radial contraction thereof for insertion of the prosthesis 10 into a blood vessel or other bodily passageway using a catheter, not shown. Although not shown in FIG. 1, the tubular conduit 12 may also be formed with one or more longitudinal crimps, creases or the like to enable folding for insertion of the prosthesis into a blood vessel via a catheter.

Figure 4:
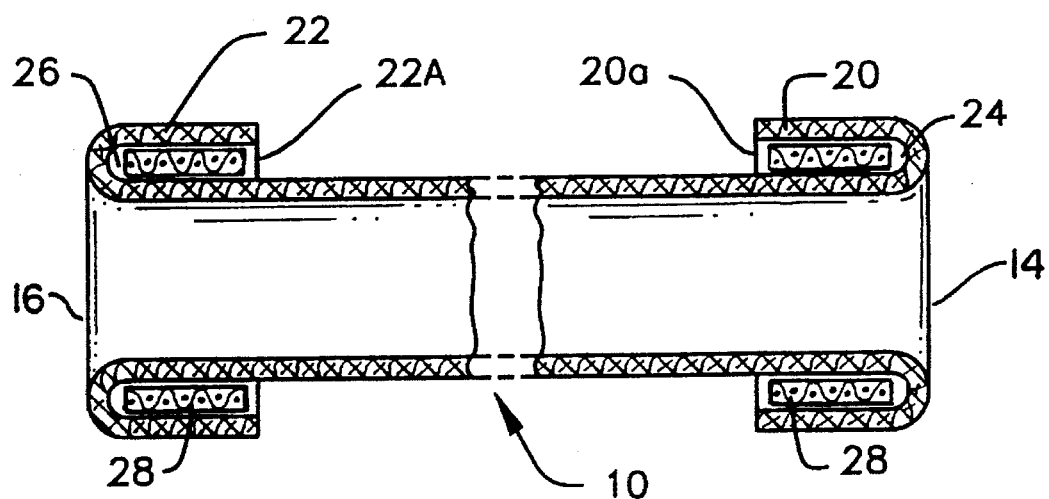
FIG. 4 shows in longitudinal cross-section the tubular prosthesis of FIG. 1 supporting a pair of stents shown in FIGS. 2 and 3.
Figure 5:
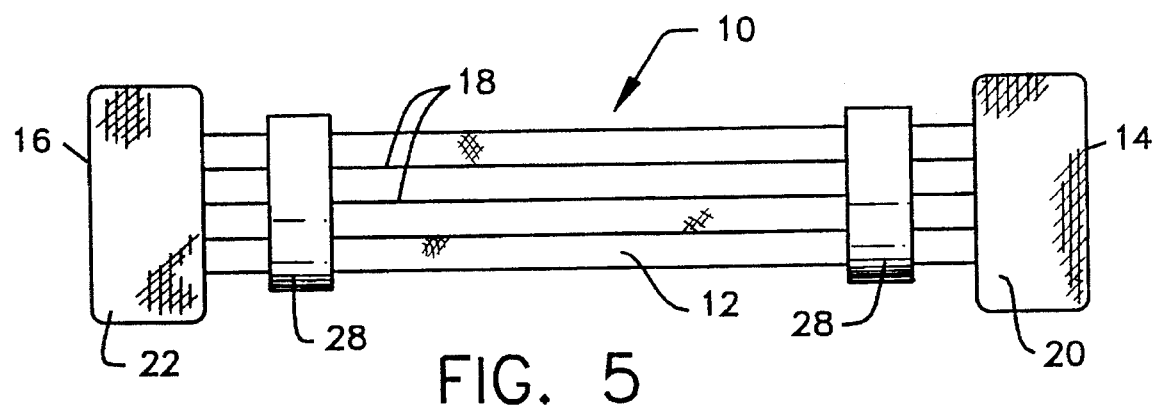
FIG. 5 is a side elevational view of the combination shown in FIG. 4.

Referring now to FIGS. 4 and 5, in accordance with the present invention tubular prosthesis 10 includes a pair of cuffs 20 and 22 disposed respectively adjacent ends 14 and 16. The cuffs 20 and 22 may be free standing cuffs, formed by folding the ends of the tubular conduit 12 back externally over itself. It is also contemplated that the cuffs may be formed by turning inwardly the ends of conduit 12. The cuffs 20 and 22 may also be formed of separate, distinct portions of synthetic material which may be glued or sutured onto tubular conduit 12. Further, the cuffs may comprise a material, such as an elastomeric material that is different than the material comprising the conduit. Cuffs 20 and 22 include inwardly directed open ends 20a and 22a respectively which are wholly unobstructed for stent insertion. Open ended slots 24 and 26 are defined between the external surface of tubular conduit 12 and the internal surface of cuffs 20 and 22. The slots 24 and 26 house one or more stents, such as stent 28, used by the device to both support and seal the body vessel into which the tubular prosthesis 10 is inserted. The stents 28 may be used whether the present invention is used as an implantable prosthetic graft or an endoprosthesis.

The accommodation of stents 28 within the slots 24 and 26 of tubular prosthesis 10 helps assure patency of the lumen of a blood vessel or other body passageway into which the prosthesis 10 is inserted at the exact place at which support is required. The prosthesis/stent combination assures a secure anchor of the prosthesis 10 to the inner lumen surface of the blood vessel due to the radially expansive properties of stent 28.

Stent 28 provides more than means for improved support and anchoring properties for the invention. Stent 28 also provides a support structure that is never in direct contact with a body fluid passing through the intraluminal passageway into which it is installed. Accordingly, fibrin and thrombotic deposits, common in prior art support structures which are in direct contact with the blood after implantation, are minimized.

The stent 28 may be inserted and positioned within either or both of cuffs 20 and 22 of prosthesis 10 before implantation. Alternatively, the stent may be inserted into the prosthesis via catheter after the prosthesis 10 has been implanted. If stents 28 are positioned within cuffs 20 and 22 prior to implantation then the stents may be radially compressed along with tubular conduit 12 for catheter deployment. However, as above mentioned, tubular body 12 with cuffs 20 and 22 may be intraluminally deployed first and then stents 28 may be inserted in a subsequent procedure. It is still further contemplated that in certain situations, the stents may be disposed over tubular conduit 12 such as shown in FIG. 5, and then once deployed the stents may be inserted into cuffs 20 and 22.

Figure 6:
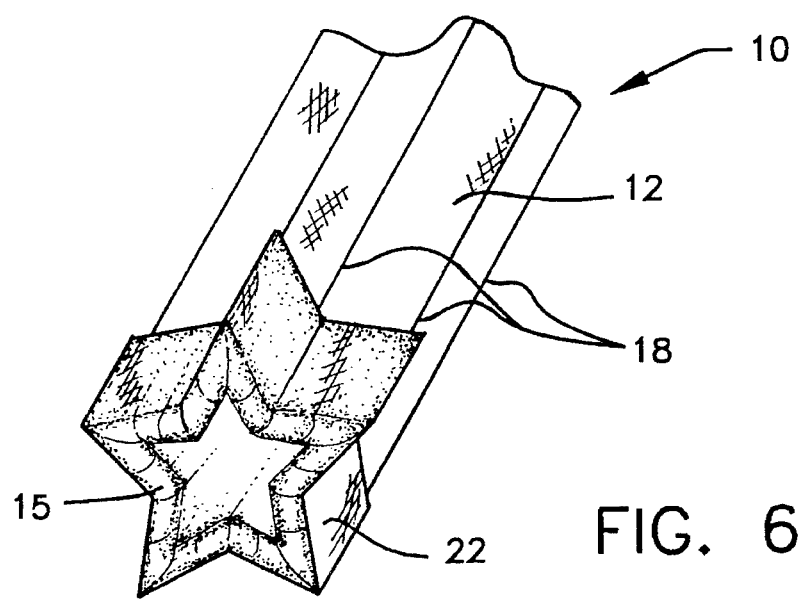
FIG. 6 is a partial perspective showing of the prosthesis of FIGS. 4 and 5 shown in a partially collapsed condition.

As mentioned above, implantable tubular intraluminal prosthesis 10 may include longitudinal ribs 18 which permit prosthesis 10 to be in partially folded or radially collapsed as shown in FIG. 6. Other techniques for collapsing prosthesis 10 may also be employed. In the radially collapsed state, where the tubular conduit 12 as well as cuffs 20 and 22 are collapsed, the intraluminal prosthesis 10 can negotiate curves or bends of a blood vessel or other body passageway in which it is implanted and transported. The device may be inserted percutaneously (in its collapsed state) by use of a delivery catheter (not shown) and directed to a target area by any means or method known to those skilled in the art. When positioned, stent 28 and tubular conduit 12 are then radially expanded to return to the condition shown in FIGS. 4 and 5. Radial expansion of both conduit 12 and stents 28 may be accomplished with assistance of, for example, an expandable catheter balloon. It is also contemplated that the conduit 12 as well as stents 28 may be constructed to be radially self-expanding after deployment.

As stents 28 are contained within the slots 24 and 26 outside the lumen of intraluminal prosthesis 10, the prosthesis has an almost infinitely variable and adjustable diameter in the ranges between the minimum and maximum diameter of the tubular conduit 12. Thus, the inner diameter of the lumen of the vessel in which the device is inserted need not be exactly known or predetermined.

Figure 7:
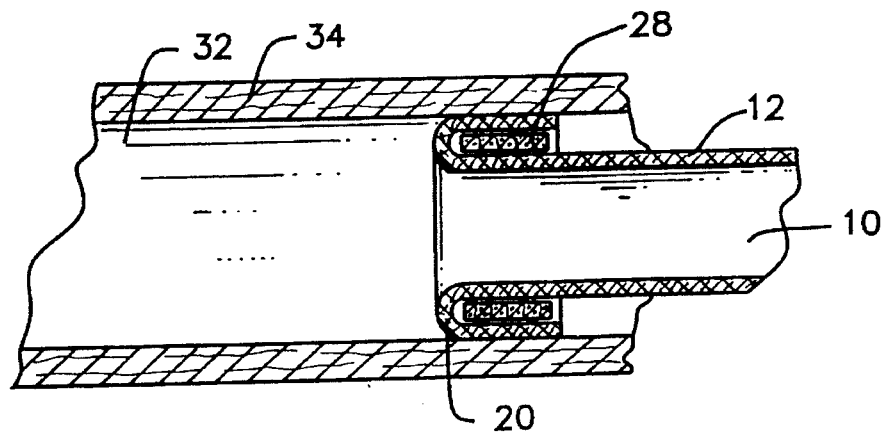
FIG. 7 is a partial sectional showing of the tubular prosthesis of the present invention implanted within a body vessel.

Referring to FIG. 7, stent 28 is designed to radially expand with the force sufficient enough to anchor prosthesis 10 within a lumen 32 of a vessel 34 to form a liquid seal therein without placing disruptive force or undue pressure on the intraluminal walls. If it is determined that a more appropriately sized stent is necessary for a proper seal after insertion, the stent can be easily removed and replaced within the cuff by a better fitting stent without first excising the prosthesis. As the cuffs are generally flexible and complaint, they may accommodate a range of stent sizes as may be dictated by the particular application.

Stent 28 is shown clearly supported in slot 24. Because the stent is enclosed between the prosthesis material of tubular body 12 and cuff material 20, the stent 28 is never in direct contact with either blood flowing through lumen 32 or the tissue of the walls of vessel 34. This is a marked improvement over conventional methods of using stents, normally attached using hooks or sutures directly to the luminal walls.

As mentioned above, while the preferred embodiment of the present invention shows an endoprosthesis which is used to reinforce or buttress a body lumen, it is also contemplated that the present invention may be practiced with a tubular graft which may be used to replace a missing section of a body lumen such as a blood vessel.

Thus, while the above embodiments have been disclosed, other and further manifestations of the present invention will become apparent to those skilled in the art. It is intended to claim all such changes and modifications which come within the true scope and spirit of the present invention.

What is claimed:

1. An implantable prosthesis comprising:
   a tubular conduit having an elongate body and opposed open ends, said conduit being capable of radial diametrical change between a first diameter and a second diameter;
   an elongate cuff formed at one end of said body said cult defining an open-ended slot between said cuff and said body;
   a variable diameter generally annular stent supported by said cuff said stent being freely insertably and removably positionable within said slot prior to or after implantation of said body.

2. An implantable prosthesis of claim i wherein said cuff defines a partial enclosure with said body for enclosing said stent.

3. An implantable prosthesis of claim 1 wherein said cuff has a closed end and an open end defining a slot for insertable accommodation of said stent.

4. An implantable prosthesis of claim 1 wherein said tubular conduit includes a plurality of longitudinal ribs to permit radial contraction from said first diameter to said second diameter to provide for intraluminal deployment.

5. An implantable prosthesis of claim 4 wherein said variable diameter stent is radially collapsible to permit intraluminal deployment thereof.

6. An implantable prosthesis of claim 5 wherein said tubular conduit is radially expandable from said second diameter to said first diameter after said intraluminal deployment.

7. An implantable prosthesis of claim 6 wherein said stent is radially expandable after said intraluminal deployment.

8. An implantable prosthesis of claim 1 wherein said tubular conduit is formed of a textile fabric.

9. An implantable prosthesis of claim 1 wherein said tubular conduit is formed from polytetrafluoroethylene.

10. An implantable prosthesis of claim 1 wherein said stent is formed of a wire mesh.

11. An implantable prosthesis of claim 1 wherein said cuff is integrally formed with said tubular conduit.

12. An implantable prosthesis of claim 11 wherein one end of said tubular conduit is folded back upon said body to form said cuff.

13. An implantable prosthesis of claim 12 wherein said one end of said tubular conduit is folded externally over said body.

14. An implantable prosthesis of claim 12 wherein said other end of said tubular conduit includes a cuff.

15. An implantable prosthesis of claim 1 wherein said cuff is compliant to accommodate said stent within a range of different stent sizes.

16. A prosthesis for implantation within a body lumen comprising:
   an elongate radially expandable tubular body;
   a pair of cuffs, one cuff formed at each end of said body; and
   a pair of radially expandable stents one stent resident in each cuff of said pair of cuffs wherein each of said cuff having an open-ended slot between said cuff and said body, and said stent being freely insertably and removably positionable within said slot prior to or after implantation of said tubular body.

17. A prosthesis of claim 16 wherein said cuffs are elongate members each having a closed end and an open end for insertion of said stent.

18. A prosthesis of claim 17 wherein said ends of said body are folded back over to form said cuffs.

19. A prosthesis of claim 18 wherein said cuffs and said tubular body define slots enclosing said stents.

20. A prosthesis of claim 16 wherein said stent is a generally annular wire mesh member.

21. A prosthesis of claim 16 wherein said tubular body is formed of a synthetic fabric.

22. A prosthesis of claim 16 wherein said tubular body is formed of polytetrafluoroethylene.

* * * * *

UNITED STATES PATENT AND TRADEMARK OFFICE
CERTIFICATE OF CORRECTION

PATENT NO. : 5,522,881
DATED : June 4, 1996
INVENTOR(S) : David J. Lentz

It is certified that error appears in the above-indentified patent and that said Letters Patent is hereby corrected as shown below:

column 5, line 54, incorrectly reads "said body said cult". Claim 1, line 6, should correctly read --said body said cuff--.

column 5, line 62, incorrectly reads "of claim i". Claim 2, line 1, should correctly read --of claim 1--.

Signed and Sealed this

Tenth Day of September, 1996

Attest:

BRUCE LEHMAN

*Attesting Officer*    *Commissioner of Patents and Trademarks*